(12) United States Patent
Jasperse (10) Patent No.: US 11,668,647 B2
(45) Date of Patent: *Jun. 6, 2023

(54) ILLUMINATION UNIT WITH MULTIPLE LIGHT SOURCES FOR GENERATING A UNIFORM ILLUMINATION SPOT

(71) Applicant: Siemens Healthcare Diagnostics Inc., Tarrytown, NY (US)

(72) Inventor: Jeffrey R. Jasperse, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/647,984

(22) Filed: Jan. 14, 2022

(65) Prior Publication Data

US 2022/0136960 A1 May 5, 2022

Related U.S. Application Data

(63) Continuation of application No. 17/051,837, filed as application No. PCT/US2019/030549 on May 3, 2019, now Pat. No. 11,262,294.

(60) Provisional application No. 62/666,913, filed on May 4, 2018.

(51) Int. Cl.
*G01N 21/25* (2006.01)
*G01N 21/31* (2006.01)
*G01N 33/49* (2006.01)

(52) U.S. Cl.
CPC .......... *G01N 21/255* (2013.01); *G01N 21/31* (2013.01); *G01N 33/491* (2013.01); *G01N 2201/061* (2013.01); *G01N 2201/062* (2013.01); *G01N 2201/0636* (2013.01); *G01N 2201/127* (2013.01)

(58) Field of Classification Search
CPC .... G01N 21/255; G01N 21/31; G01N 33/491; G01N 2201/061; G01N 2201/062; G01N 2201/0636; G01N 2201/127; G01N 21/274; G01N 2021/3144; G01J 3/0291; G01J 2003/102; G01J 3/0256; G01J 3/10; G01J 3/0229; G02B 5/005; G02B 27/143
USPC ........................................................ 356/405
See application file for complete search history.

(56) References Cited

U.S. PATENT DOCUMENTS

| | | | |
|---|---|---|---|
| 5,340,716 A | 8/1994 | Ullman et al. |
| 5,709,994 A | 1/1998 | Pease et al. |
| 5,807,675 A | 9/1998 | Davalian et al. |
| 6,069,689 A | 5/2000 | Zeng et al. |

(Continued)

FOREIGN PATENT DOCUMENTS

| | | |
|---|---|---|
| CN | 104267506 A | 1/2015 |
| DE | 102012010406 A1 | 3/2013 |

(Continued)

OTHER PUBLICATIONS

International Search Report and Written Opinion of International Application No. PCT/US2019/030549 dated Jul. 23, 2019.

(Continued)

*Primary Examiner* — Md M Rahman (57) ABSTRACT

An illumination unit is described that includes a first light source positioned on a first axis and a second light source on a second axis that intersects and is angularly offset with respect to the first axis. The illumination unit includes a reflector having an aperture through which the first axis extends and a reflective surface angled with respect to the first axis and second axis.

30 Claims, 7 Drawing Sheets

(56) References Cited

U.S. PATENT DOCUMENTS

| | | |
|---|---|---|
| 9,927,458 B2 | 3/2018 | Bramhavar |
| 11,067,527 B2 | 7/2021 | Samproni |
| 2002/0181233 A1 | 12/2002 | Adler et al. |
| 2003/0231498 A1 | 12/2003 | Lu et al. |
| 2005/0017313 A1 | 1/2005 | Wan |
| 2008/0094854 A1 | 4/2008 | Coleman |
| 2008/0274554 A1 | 11/2008 | Stimpfl et al. |
| 2008/0316463 A1 | 12/2008 | Okada et al. |
| 2010/0150779 A1 | 6/2010 | Chow et al. |
| 2010/0277695 A1 | 11/2010 | Luther et al. |
| 2015/0268159 A1 | 9/2015 | Tabaru et al. |
| 2016/0169814 A1 | 6/2016 | Hashimoto |
| 2016/0187634 A1 | 6/2016 | Krampert et al. |

FOREIGN PATENT DOCUMENTS

| | | |
|---|---|---|
| EP | 2752701 A1 | 7/2014 |
| JP | 2000097657 A | 4/2000 |
| JP | 2001050899 A | 2/2001 |
| JP | 2004021259 A | 1/2004 |
| JP | 2008275625 A | 11/2008 |
| JP | 2011175735 A | 9/2011 |
| WO | 2009157098 A1 | 12/2009 |
| WO | 2014109126 A1 | 7/2014 |

OTHER PUBLICATIONS

European Search Report and Written Opinion of European Application No. 19795795.4 dated Jun. 15, 2021.

ILLUMINATION UNIT WITH MULTIPLE LIGHT SOURCES FOR GENERATING A UNIFORM ILLUMINATION SPOT

The subject application is a continuation of U.S. Ser. No. 17/051,837, filed Oct. 30, 2020; which is a US national stage application filed under 35 USC § 371 of International Application No. PCT/US2019/030549, filed May 3, 2019; which claims benefit under 35 USC § 119(e) of U.S. provisional Application No. 62/666,913, filed May 4, 2018. The entire contents of each of the above-referenced patent applications are hereby expressly incorporated herein by reference.

TECHNICAL FIELD

The present disclosure relates to an illumination unit with multiple light sources for generating a uniform illumination spot.

BACKGROUND

Various types of tests related to patient diagnosis and therapy can be performed by analysis of a sample, such as a patient's bodily fluids. These tests typically use automated sample analyzers onto which vials containing samples have been loaded. The sample analyzer extracts the samples from the vials and combines the samples with various reagents in reaction vessels. Frequently, the samples are incubated or otherwise processed before being analyzed. Such sample analyzers obtain measurements from the sample in order to determine the presence and/or amount of analyte of interest. Although various known clinical analyzers for chemical, immunochemical and biological testing of samples are available, analytical clinical technology is challenged by increasing needs for improved levels of analysis. The improvement of analytical sensitivity continues to be a challenge.

Typical sample analyzers use an optical system during the test procedure to obtain readings from the sample. A typical optical system has an aligned light source and a detector (e.g. spectrophotometer). The sample vessel contains the sample and a reagent and is positioned between the light source and detector along an optical axis centerline of the light source. The light source emits light into the input region into the sample-reagent combination inside the vessel. A chemical reaction of the sample-reagent combination produces chromophores absorbing light at specific wavelengths proportional to the concentration of the analyte being measured. Light emitted from the illuminated sample-reagent combination inside the vessel exits the output region and is detected by the detector. The detector obtains an absorbance measurement of the emitted light signal at specific wavelengths following the Beer-Lambert law. In addition to absorbance readings, other readings may be obtained, such as turbidimetric, fluorometric and like readings. The obtained readings are used to determine an amount of analyte in the sample using well-known calibration techniques.

SUMMARY

An embodiment of the present disclosure is an illumination unit. The illumination unit includes a housing assembly that defines an internal space. The illumination unit includes a first light source mounted to the housing assembly in the internal space. The first light source is positioned on a first axis. The illumination system includes a second light source mounted to the housing assembly in the internal space on a second axis that intersects and is angularly offset with respect to the first axis. The illumination unit includes a reflector in the internal space of the housing assembly, the reflector including an aperture through which the first axis extends and a reflective surface angled with respect to the first axis and the second axis, and an optional lens positioned in the housing assembly and positioned on the first axis opposite the reflector.

Another embodiment of the present disclosure is an illumination unit. The illumination unit includes a first light source positioned on a first axis and a second light source positioned on a second axis that intersects and is angularly offset with respect to the first axis. The illumination unit also includes a reflector positioned on the first and second axes. The reflector has an elliptical aperture through which the first axis extends and a reflective surface. The reflective surface is angled with respect to the first axis and the second axis such that light traveling from the first light source through the elliptical aperture creates a circular beam of light on a target positioned on the first axis opposite the first light source relative to the reflector.

BRIEF DESCRIPTION OF THE DRAWINGS

The foregoing summary, as well as the following detailed description of the illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. In the drawings.

DETAILED DESCRIPTION OF THE ILLUSTRATIVE EMBODIMENTS

Figure 1:
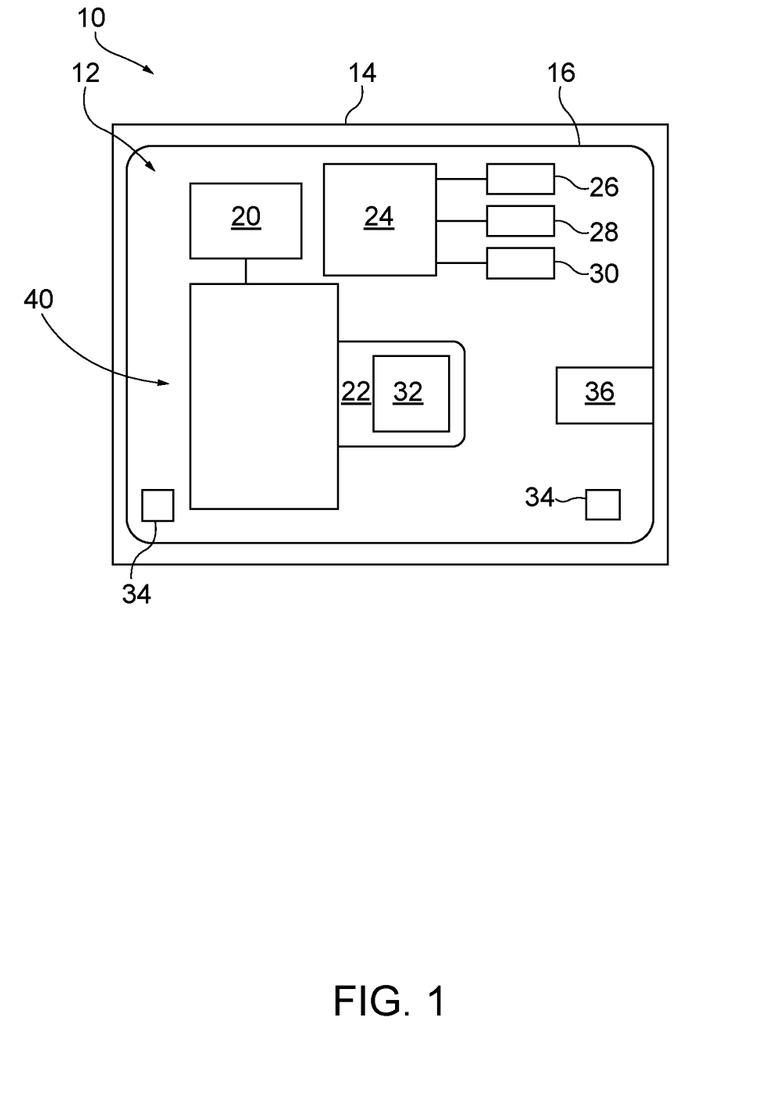
FIG. 1 is a schematic plan view of a sample analysis system according to an embodiment of the present disclosure.
Figure 2A:
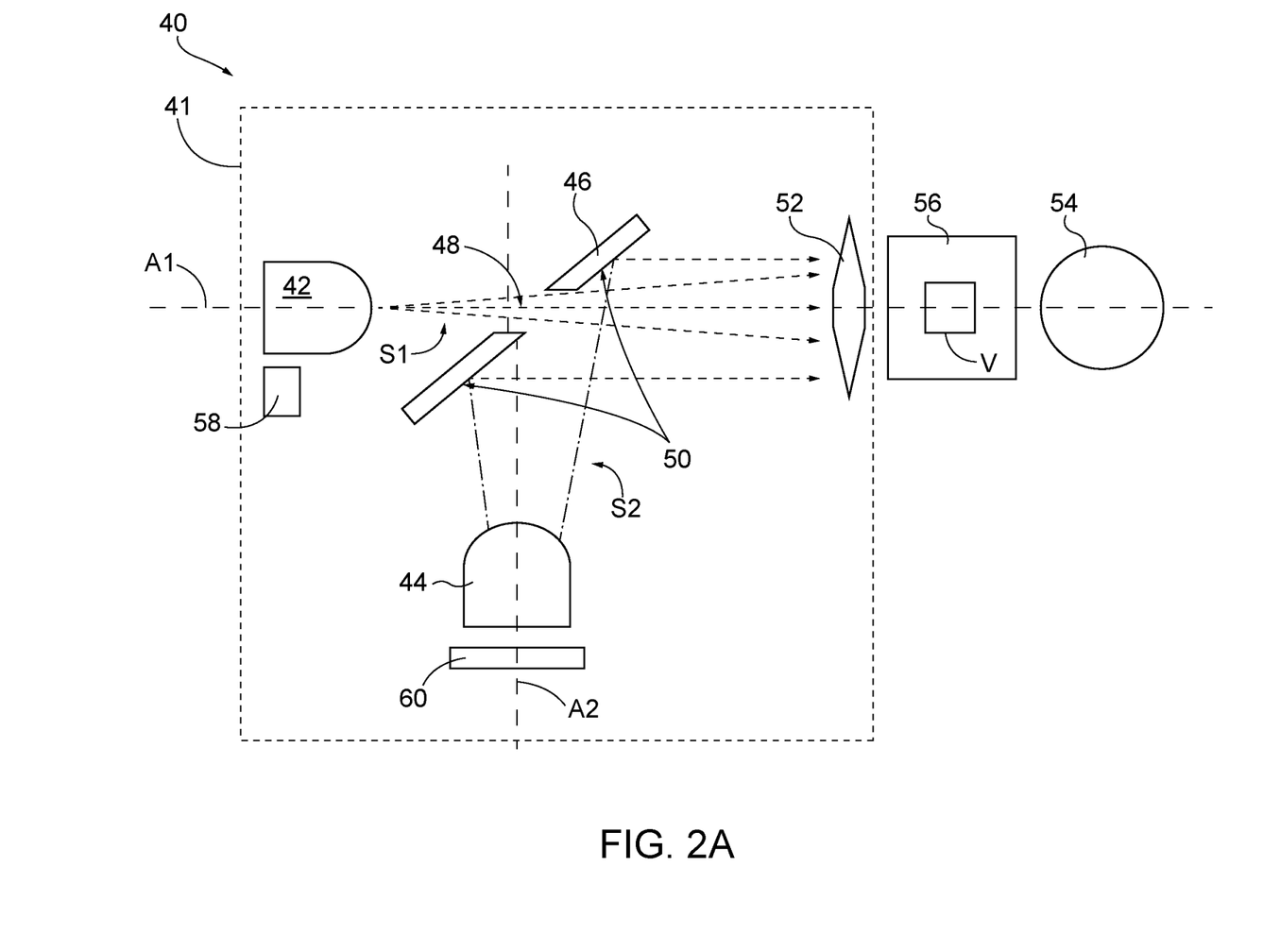
FIGS. 2A and 2B are schematic plan views of an illumination unit in the sample analysis system illustrated in FIG. 1.
Figure 2B:
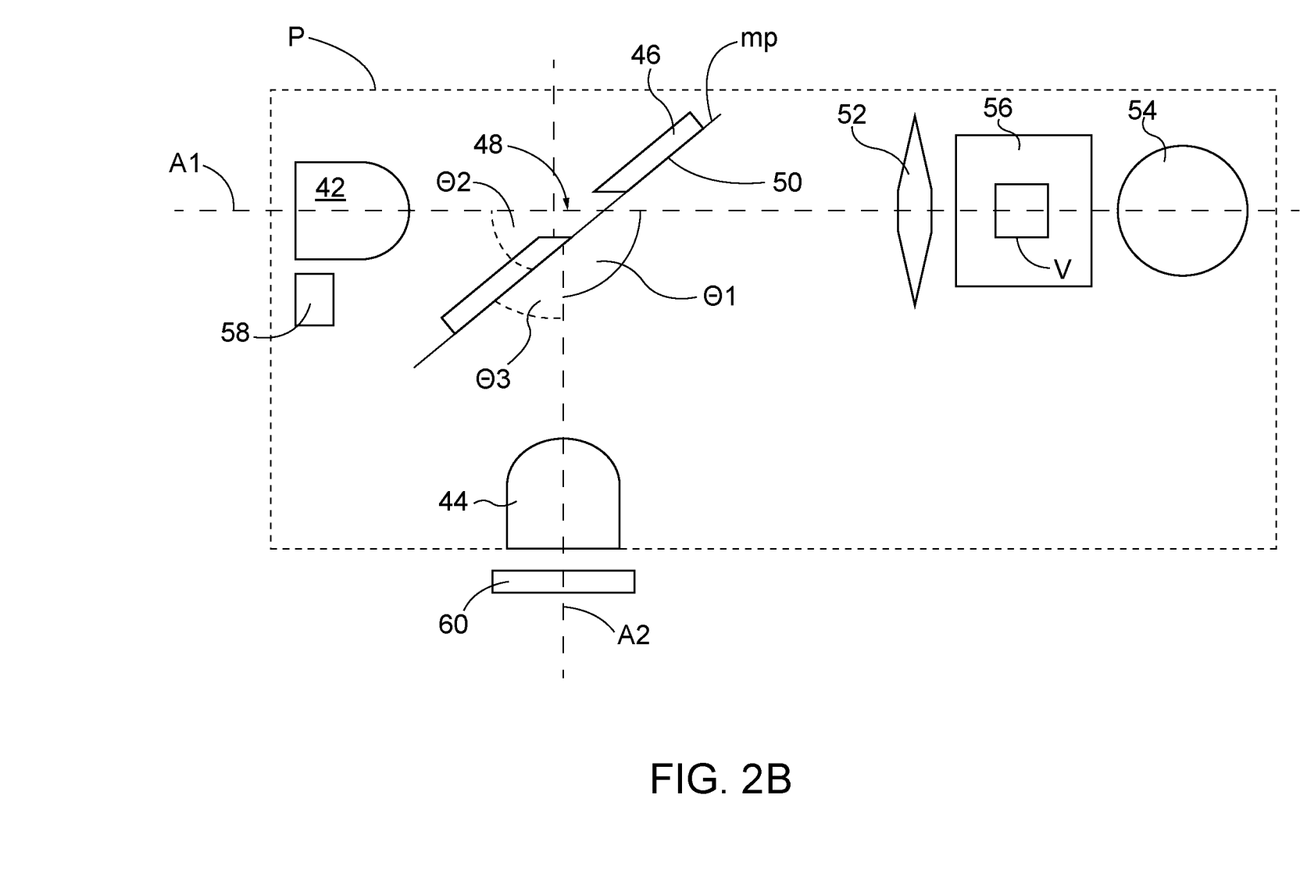

Referring to FIGS. 1-2B, embodiments of the present disclosure include an illumination unit that may be used within a sample analysis system 10 adapted to analyze a sample S. While the illumination unit is described below with respect to a sample analysis system, the illumination unit may have other applications and uses.

In an embodiment, the sample analysis system 10 includes a sample analyzer 12 and a sample vessel V. The sample vessel V is designed to hold a sample S for analysis by the sample analyzer 12 as will be detailed further below. The sample S can be any type of liquid. For example, the sample S can be a biological sample or body fluid, such as blood, plasma, urine, or other fluids obtained from a patient. Furthermore, the sample S may also include non-biological sample liquids. The sample S is not limited strictly to liquids obtained from the patient. The illumination unit is configured to generate a substantially uniform light spot on a target T. For example, the target T could be a sample vessel V as shown. The uniform light spot may be generated by using multiple sources of light, offset with respect to each other, as will be described further below.

The sample analyzer 12 includes an analyzer housing 14 and a mechanical stage 16 in the analyzer housing 14 that supports various components of the sample analyzer 12. The sample analyzer 12 includes a detection unit 40 that holds the sample vessel V and can analyze the sample S in the sample vessel V, and a controller 20 that controls operation of the detection unit 40. A thermal plate 22 may be used to support the detection unit 40 and to incubate the sample S in the sample vessel V. Additional heating elements (not shown) may be placed proximate the sides of the sample vessel V to heat the sample S as needed. A dispensing device 24 may be included to dispense a sample from a sample vial, and/or reagent, into the sample vessel V. The dispensing device 24 includes a motor 26 that powers the dispensing device 24, a pump 28, and a valve 30, such as a lee valve. In certain embodiments, such as for sample analyzers adapted to analyze blood and/or plasma samples, a plasma separator 32 may be included to separate plasma from the blood sample for analysis. The sample analyzer 12 may further include one or more position sensors 34 used to determine the position of the stage 16 and/or detection unit 40 with respect to the dispensing device 24. A vacuum port 36 may be included to control pressure in the housing 14.

The sample analyzer 12 illustrated in FIG. 1 is an exemplary sample analyzer that illustrates inventive concepts set forth in the present disclosure. The sample analyzer 12 as described herein can be any type of sample analyzer adapted to make measurements of the sample S illuminated in a sample vessel. In one embodiment, the sample analyzer can be adapted to determine an analyte level in a highly sensitive assay format known as a Luminescent Oxygen Channeled Immunoassay (LOCI), such as the analyzers disclosed in U.S. Pat. Nos. 5,340,716 and 5,709,994, incorporated herein by reference. In another example, the sample analyzer is adapted to determine an analyte level in a less sensitive assay format known as a Fluorescent Oxygen Channeled Immunoassay (FOCI) using a photosensitizer, such as the analyzer disclosed in U.S. Pat. No. 5,807,675, incorporated herein by reference. It should also be appreciated that the sample analyzer can be adapted to analyze multiple samples. In one example, the sample analyzer may include a cartridge adapted to hold a plurality of sample vessels V. In yet another example, the sample analyzer may be an automated analyzer that includes a moveable carousel for holding multiple sample vessels. Such an analyzer may include multiple detection units testing for different analytes of interest. An exemplary automated analyzer is disclosed in U.S. Patent App. Pub. No. 2010/0150779, incorporated herein by reference. Other exemplary sample analyzers include the ADVIA® and DIMENSION® analyzers (Siemens Healthcare Diagnostics Inc.).

Referring to FIGS. 1-2B, the detection unit 40 includes an illumination unit 41. The illumination unit 41 may include multiple lights sources 42 and 44, a reflector 46, and at least one lens 52. It should be appreciated that in some embodiments, the illumination unit 41 may not include a lens 52. Accordingly, the lens 52 is an optional component. In one example, the illumination unit 41 may be self-contained, e.g. in a separate housing, in order to be easily removed from the sample analyzer 12. As illustrated, the illumination unit 41 includes a first light source 42 on the first axis A1 and a second light source 44 on a second axis A2 that intersects and is angularly offset with respect to the first axis A1. The first light source 42 is configured to emit a first light signal S1 along the first axis A1. The second light source 44 is configured to emit a second light signal S2 along the second axis A2. In the example shown, the first axis A1 and the second axis A2 intersect at about 90 degrees. However, the positions of the first and second light sources may be different from 90 degrees as will be further detailed below. The first light source may be a light emitting diode and the second light source may be a neon lamp. In one example, the first light source 42 is adapted to emit a light of specified wavelength into the sample S contained in the sample vessel V. For instance, the first light source 42 may have light signal with a broadband white light 450 nm to 680 nm. Furthermore, the second light source 44 may have light signal with a neon lamp gas line source at 585.249 nm for spectrometer calibration. The result of such an embodiment is an even spot intensity profile on the target for both light sources. However, in certain implementations, the first light source need not be an LED and/or the second light source need not be a neon lamp.

As described above, the illumination unit 41 also includes a reflector 46. The reflector 46 has an aperture 48 through which the first optical axis A1 extends, and a reflective surface 50 that is angled with respect to the first axis A1 and the second axis A2. A lens 52 is positioned on the first optical axis A1 opposite the reflector 46. One lens is shown but more may be included, or as discussed above, no lens may be included. A detector 54 may be aligned with the lens 52 on the first axis A1 and spaced from the lens 52 as shown. While the detector 54 is shown adjacent the lens 52, the detector 54 may be in located in other positions, consistent with teachings of the present disclosure. Furthermore, the detector 54 may be separate from the illumination unit 41 or a component of it. The detector 54 may be a spectrophotometer as is known in the art.

Figure 2C:
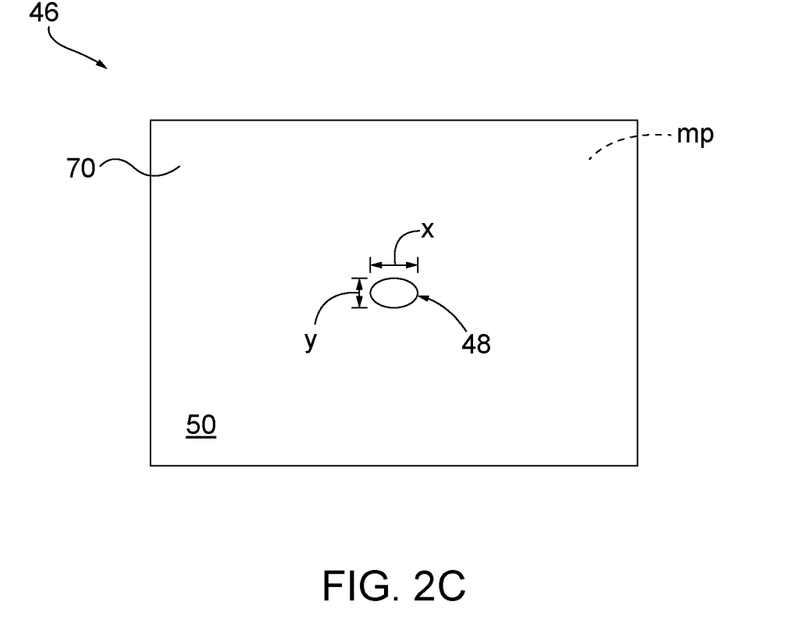
FIG. 2C is a front elevation view of a reflector in the illumination unit shown in FIGS. 2A and 2B.
Figure 2D:
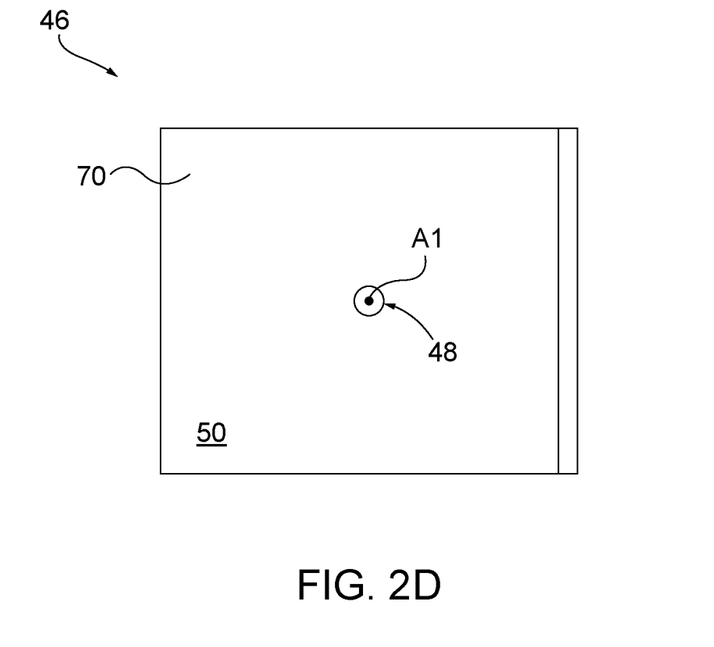
FIG. 2D is a view of the reflector in the illumination unit shown in FIGS. 2C, angled so the viewing angle is along a first axis A1 of the light source shown in FIGS. 2A and 2B.
Figure 3:
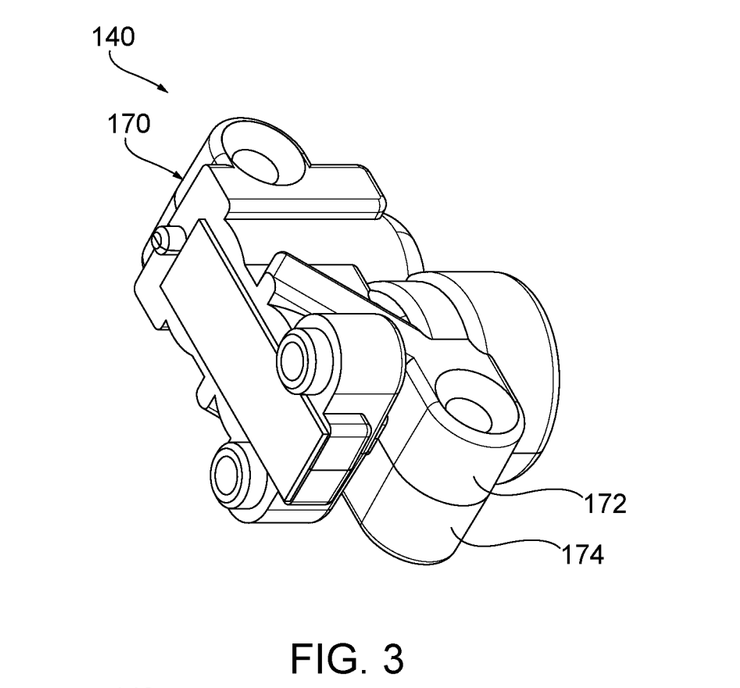
FIG. 3 is a perspective view of an illumination unit and its housing assembly in the sample analysis system according to an embodiment of the present disclosure.
Figure 4:
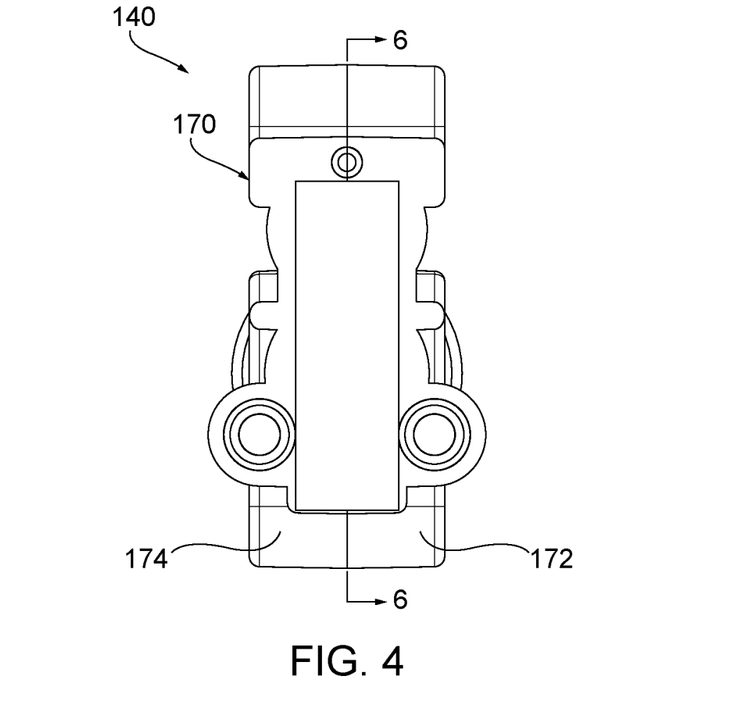
FIG. 4 is a side view of the illumination unit illustrated in FIG. 3.
Figure 5:
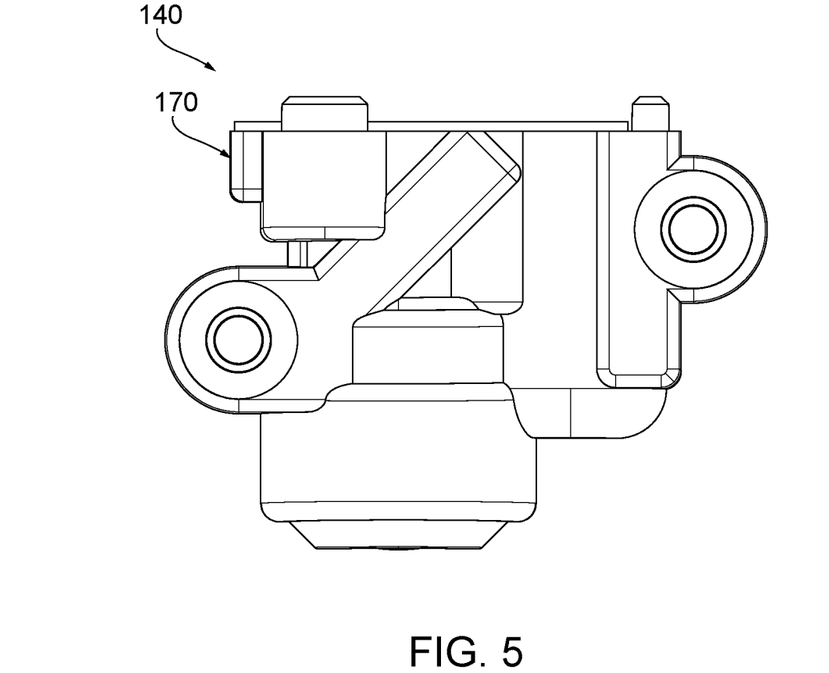
FIG. 5 is a top view of the illumination unit illustrated in FIG. 3.

An embodiment of the reflector 46 is shown in FIGS. 2C and 2D. The reflector 46 has a body 70 which includes the reflective surface 50. The aperture 48 is defined by the body 70 of the reflector 46 and extends entirely through the body 70. The reflective surface 50 lies along a reflector plane MP. As illustrated in FIG. 2C, when viewed from a position parallel to the reflector plane MP, the aperture 48 has an elliptical shape. Accordingly, the body 70 may define a major dimension X of the aperture 48 and a minor dimension Y of the aperture 48 that is perpendicular to and intersects the major dimension X. The size of the elliptical aperture may vary with the major dimension X ranging between 0.5 mm up to 5 mm and the minor dimension Y ranging between 0.5 mm up to 4.0 mm. It should be appreciated that these ranges are not limiting and that both major and minor dimensions may be more than the lower limits or higher than the upper limits disclosed above. However, when the reflector 46 is positioned in the illumination unit, the reflector 46 is angled with respect to the first light source 42. As can be seen in FIG. 2D, when the reflector 46 is angled in this manner, such that first axis A1 extends through the aperture 48 and is angled with respect to reflector plane MP, the observable shape of the aperture 48 is circular. Thus, light passing through the aperture 48 from the first light source 42 toward target T has a circular shaped light beam in cross-section. As will be explained below, the aperture shape and angled position help generate a uniform spot profile on the target. The illustrated reflector 46 has a planar shape. In other embodiments, however, the reflector could have a conical shape or a semi-spherical or dome shape. In embodiments of the present disclosure, the multiple light sources and apertured reflector design address the problem of getting the full spectral range of the white light source 42 to the target without attenuating any wavelengths.

A sample vessel holder 56 may be included that is configured to hold a sample vessel V. The sample vessel holder 56 is located adjacent the detector 54 on the first optical axis A1. However, the sample holder 56 and detector 54 may be arranged in configurations other than those specifically shown in the drawings. The first and second light sources 42 and 44 emit light into the sample in the vessel V and the detector 54 detects the luminescence of the sample S that exits sample vessel V.

A light sensor 58 is positioned proximate the first light source 42 and is configured to monitor the intensity of the first light signal S1 emitted from the first light source 42. In addition, the illumination unit 41 may include another reflector 60 positioned adjacent to the second light source 44 opposite the reflector 46. The illumination unit 41 may include an optional filter and a polarizer (not shown).

Referring to FIGS. 2A and 2B, the first light source 42, the second light source 44, and the reflector 46 may be arranged with respect to each other to generate a uniform spot illumination on the target T in operation. As best illustrated in FIG. 2B, the first light source 42, the second light source 44, the reflector 46 lie along a common plane P that includes the first axis A1 and the second axis A2. The first axis A1 and the second axis A2 intersect to define an angle θ1. In one example, angle θ1 is between 45 degrees and 135 degrees. In one example, the angle θ1 is between 75 degree and 105 degrees. In another example, the angle θ1 is about 90 degrees.

The reflector 46 is angled with respect to the first and second light sources 42 and 44 to direct emitted light toward the target T. As shown in FIGS. 2A and 2B, the reflective surface 50 is disposed along the reflector plane MP. The reflector plane MP and the first axis A1 define a first reflector angle θ2 that is less than about 90 degrees. In one example, the first angle is between 15 degrees and 75 degrees. In one example, the first reflector angle θ2 is about 45 degrees. The reflector plane MP and the second axis A2 define a second reflector angle θ3 that is less than about 90 degrees. In one example, the second reflector angle θ3 is between 15 degrees and 75 degrees. In one example, the second reflector angle θ3 is about 45 degrees. The sum of the first reflector angle θ2 and the second reflector angle θ3 may be about 90 degrees in one example. However, this sum may vary based on the position of the first and second light sources 42 and 44. It should be appreciated that the first reflector angle θ2 and the second reflector angle θ3 are related. As one angle increases, the other angle decreases, depending on the arrangement of the first and second light sources 42 and 44. It should be appreciated that that this configuration permits multiple light sources to be mounted on the same printed circuit board (PCB) with the reflector 46. This, in turn, can permit designs with removable housings that would allow for easy and simple replacement of the illumination unit as needed.

As illustrated in FIGS. 2A and 2B, the first and second light sources 42 and 44 are arranged on a common plane P with the detector 54. However, the first and second light sources 42 and 44 can be positioned with respect to each different from what is illustrated in the figures. For instance, the second light source 44 may be positioned above the plane P that contains the first light source 42 and the detector 54. In such an example, the second light source 44 is aligned along the second axis A2 that, while still intersecting the first axis A1, defines an angle greater than 0 degrees with respect to the common plane P described above. Accordingly, the second light source 44 can be positioned above (with respect to FIGS. 2A and 2B) the first light source 42.

In still other embodiments, multiple sets of each light source may be used. For instance, the illumination unit 41 may include a plurality of first light sources and a plurality of second light sources. In still other embodiments, there may be included a first light source 42, such as an LED, and a plurality of second light sources 44, such as a plurality of neon lamps.

Figure 6A:
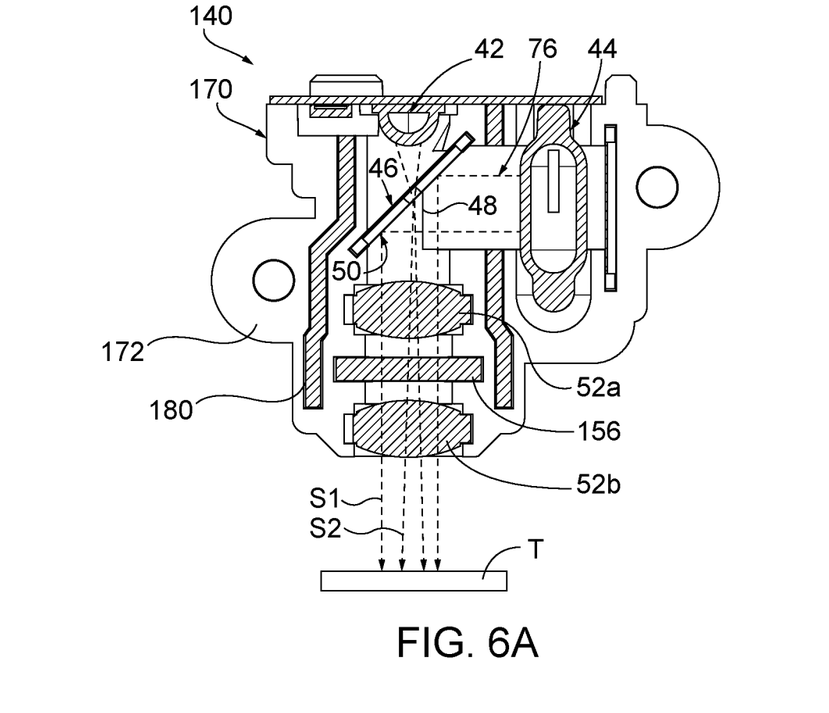
FIG. 6A is a cross-section of the illumination unit taken along line 6-6 in FIG. 4.
Figure 6B:
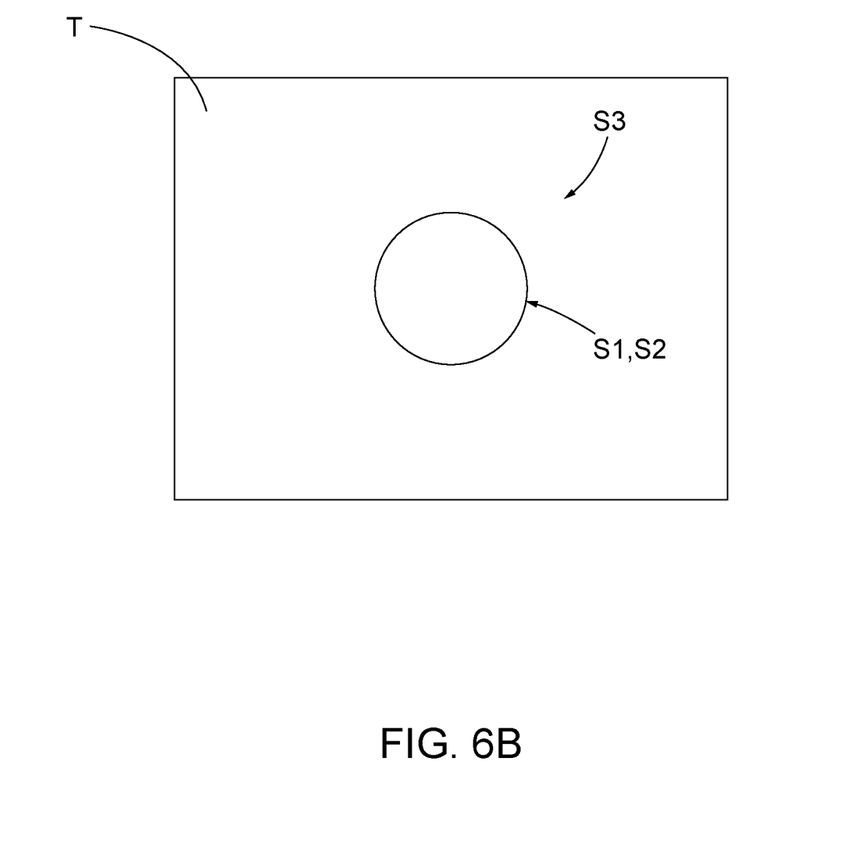
FIG. 6B is an elevation view of the target shown in FIG. 6A and illustrating the light signals generating a uniform spot on the target.

Turning to FIGS. 3-6B, an embodiment of the disclosure includes an illumination unit 140. The illumination unit 140 is substantially similar to and has features common with the illumination unit 41 described above. Accordingly, the same reference signs will be used for features that are common between illumination unit 41 and illumination unit 140. In accordance with the embodiment shown in FIGS. 3-6, the illumination unit 140 has an optional housing assembly 170 that contains at least the first light source 42, the reflector 46, the second light source 44, an optional first lens 52a, and an optional second lens 52b. The illumination unit may include an optional filter 156. The housing assembly 170 may include a first body component 172 and a second body component 174. Together, the first and second body components 172 and 174 define an internal space 76 (FIG. 6) that contains various components of the illumination unit 140. As best shown in FIG. 6, the first body component 172 includes a housing wall 180 that both defines the internal space 76 and forms various features holding the first light source 42, the reflector 46, the second light source 44, and the optional lenses 52a, 52b in place. The wall 180 can also serve as a light seal feature. Furthermore, the wall 180 may also include various passages and terminals for coupling the illumination unit 140 to the sample analyzer. Although not shown, the illumination unit 140 may have one or more electronic connectors that may be coupled to the control board of the sample analyzer. In this regard, the illumination unit 140 is designed so that it can be removed from the sample analyzer 12 for repair or replacement without substantially disturbing other components of the sample analyzer 12. The illumination unit 140 may be positioned within an analyzer so that the lens 52 (when present) is in line with a target T, such as a sample vessel holder (not shown) and aligned with detector (not shown). The illumination unit 140 may include first and second light sources 42 and 44 arranged with respect to each other as described above with respect to illumination unit 41 and shown in FIGS. 2A and 2B. As shown in FIGS. 6A and 6B, the first and second light sources 42 and 44 generate a uniform light spot S3 on a target T, as a result of light from the first light source 42 passing through the aperture and light from the second light source 44 being reflected off of the reflective surface.

In operation of either embodiment of the illumination unit 41 or 140, the first light signal S1 passes through the aperture 48 toward the detector 54 along the first optical axis A1 and the second light signal S2 reflects off of the reflective surface 50 toward the detector 54. The aperture 48 focuses the first light signal from the first light source 42 in a region that includes the sample vessel V. The second light signal S2 is reflected toward the same region. However, the result of these two lights sources being arranged the way they are is substantially uniform light intensity spot in the region at the sample vessel. The uniformity of the light intensity can improve signal detection and resultant data compared to system with less uniform light intensity. In other words, the improved, uniform light intensity for a given region of focus improves signal accuracy on the detection side.

Embodiments of the present disclosure address the interesting problem of creating a uniform spot with proper centration and even profile across the target using multiple light sources that are physically spaced apart from each other at a considerable distance. The embodiments address this problem via use of the angled reflector and aperture in the reflector to center the first light signal, while the second light signal, from a source such as neon lamp, is reflected toward the target to create a fairly uniform and focused illumination spot on the target. In Co-Oximetry absorbance spectra measurement systems, for example, for analysis of blood O2Hb, HHb, COHb, MetHb, SulfHb, Fetal Hb and Bilirubin, a broadband white light source of approximately 450 nm to 680 nm is necessary to illuminate the blood sample to perform the absorbance measurement. While halogen lamps have typically been used to serve this purpose in the past, white light emitting diodes (LED) have been employed more recently. The light source must produce contiguous radiation across the spectrum because many wavelengths are used. In addition to this, a precision spectral line light source is needed to calibrate the spectrometer. A neon gas lamp is a workable solution producing a number of precision spectral lines; one of the lines at 585.2488 nm is particularly useful because it is in the midrange of the total spectrum, and it is produces strong intensity relative to the many other lines allowing shorter integration times to be used. The neon line calibration light source is turned on and off to periodically calibrate the spectrometer before a measurement is made, which improves measurement precision.

The invention as described in the present disclosure is capable of exploitation in industry in accordance with how it can be made and/or used.

Those skilled in the art will also appreciate that the present disclosure may be applied to other applications and may be modified without departing from the scope of the present disclosure. Accordingly, the scope of the present disclosure is not intended to be limited to the exemplary embodiments described above, but only by the appended claims.

The following is a number list of non-limiting, illustrative embodiments of the inventive concept disclosed herein:

1. A system, comprising:
a first light source on a first axis, the first light source configured to emit a first light signal along the first axis;
a second light source on a second axis that intersects and is angularly offset with respect to the first axis, the second light source configured to emit a second light signal along the second axis; and
a reflector having an aperture through which the first axis extends and a reflective surface angled with respect to the first axis and the second axis;
wherein a) the first light source is adapted to emit the first light signal through the aperture toward the detector along the first axis, and b) the second light source is adapted to emit the second light signal along the second axis to the reflective surface such that the second signal is reflected toward the detector along the first axis.

2. The system according to illustrative embodiment 1, further comprising: a sample vessel holder configured to hold a sample vessel, the sample vessel holder positioned between the lens and the detector on the first axis.

3. The system according to illustrative embodiment 1 or embodiment 2, wherein the first light source is a light emitting diode.

4. The system according to any one of the illustrative embodiments 1 to 3, wherein the second light source is a neon lamp.

5. The system according to any one of the illustrative embodiments 1 to 4, wherein the reflective surface is disposed along a reflector plane, the reflector plane and the first axis defining a first angle that is less than about 90 degrees.

6. The system according to illustrative embodiment 5, wherein the first angle is between 15 degrees and 75 degrees.

7. The system according to any one of the illustrative embodiments 1 to 6, wherein the reflective surface is disposed along a reflector plane, the reflector plane and the second axis defining a second angle that is less than about 90 degrees.

8. The system according to any one of the illustrative embodiments 1 to 7, wherein the second angle is between 15 degrees and 75 degrees.

9. The system according to any one of the illustrative embodiments 1 to 8, wherein the first axis and the second axis intersect to define an angle that is between 45 degree and 135 degrees.

10. The system according to any one of the illustrative embodiments 1 to 8, wherein first light source and the second light source, lie in a common plane that includes the first axis.

11. The system according to any one of the illustrative embodiments 1 to 10, further comprising: a reflector positioned adjacent to the second light source opposite the mirror.

12. The system according to any one of the illustrative embodiments 1 to 11, further comprising: a light sensor positioned proximate the first light source and configured to monitor the intensity of the first light signal emitted from the first light source.

13. The system according to any one of the illustrative embodiments 1 to 12, further comprising: a removable housing assembly that contains at least the first light source, the reflector, the second light source, and a lens positioned on the first axis opposite the reflector.

14. The system according to any one of the illustrative embodiments 1 to 13, further comprising: a controller to control operation of the first light source and the second light source.

15. An illumination unit, comprising:
a housing assembly that defines an internal space;
a first light source mounted to the housing assembly in the internal space, the first light source positioned on a first axis;
a second light source mounted to the housing assembly in the internal space and positioned on a second axis that intersects and is angularly offset with respect to the first axis; and
a reflector in the internal space of the housing assembly, the reflector including an aperture through which the first axis extends and a reflective surface angled with respect to the first axis and the second axis.

16. The illumination unit according to illustrative embodiment 15, wherein the first light source is a light emitting diode.

17. The illumination unit according to any one of the illustrative embodiments 15 or 16, wherein the second light source is a neon lamp.

18. The illumination unit according to any one of the illustrative embodiments 15 to 17, wherein the reflective surface is disposed along a reflector plane, the reflector plane and the first axis defining a first angle that is less than about 90 degrees.

19. The illumination unit according to illustrative embodiment 18, wherein the first angle is between 15 degrees and 75 degrees.

20. The illumination unit according to any one of the illustrative embodiments 15 to 19, wherein the reflective surface is disposed along a reflector plane, the reflector plane and the second axis defining a second angle that is less than about 90 degrees.

21. The illumination unit according to any one of the illustrative embodiments 15 to 20, wherein the second angle is between 15 degrees and 75 degrees.

22. The illumination unit according to any one of the illustrative embodiments 15 to 21, wherein the first axis and the second axis intersect to define an angle that is between 45 degree and 135 degrees.

23. The illumination unit according to any one of the illustrative embodiments 15 to 22, wherein first light source and the second light source lie in a common plane that includes the first axis.

24. The illumination unit according to any one of the illustrative embodiments 15 to 23, further comprising: a reflector positioned adjacent to the second light source opposite the reflector.

25. The illumination unit according to any one of the illustrative embodiments 15 to 24, further comprising: a light sensor positioned proximate the first light source and configured to monitor the intensity of the first light signal emitted from the first light source.

26. An illumination unit, comprising:
a first light source positioned on a first axis;
a second light source positioned on a second axis that intersects and is angularly offset with respect to the first axis; and
a reflector positioned on the first and second axes, the reflector having an elliptical aperture through which the first axis extends and a reflective surface, the reflective surface being angled with respect to the first axis and the second axis such that light traveling from the first light source through the elliptical aperture creates a circular beam of light on a target positioned on the first axis opposite the first light source relative to the reflector.

27. The illumination unit according to illustrative embodiment 26, further comprising a lens positioned on the first axis opposite the reflector.

28. The illumination unit according to illustrative embodiment 26 or 27 illustrative embodiment 14, wherein the first light source is a light emitting diode.

29. The illumination unit according to any one of the illustrative embodiments 26 to 28, wherein the second light source is a neon lamp.

30. The illumination unit according to any one of the illustrative embodiments 26 to 29, wherein the reflective surface is disposed along a reflector plane, the reflector plane and the first axis defining a first angle that is less than about 90 degrees.

31. The illumination unit according to illustrative embodiment 28, wherein the first angle is between 15 degrees and 75 degrees.

32. The illumination unit according to any one of the illustrative embodiments 16 to 31, wherein the reflective surface is disposed along a reflector plane, the reflector plane and the second axis defining a second angle that is less than about 90 degrees.

33. The illumination unit according to any one of the illustrative embodiments 26 to 32, wherein the second angle is between 15 degrees and 75 degrees.

34. The illumination unit according to any one of the illustrative embodiments 26 to 33, wherein the first axis and the second axis intersect to define an angle that is between 45 degree and 135 degrees.

35. The illumination unit according to any one of the illustrative embodiments 26 to 34, wherein first light source and the second light source lie in a common plane that includes the first axis.

36. The illumination unit according to any one of the illustrative embodiments 26 to 35, further comprising another reflector positioned adjacent to the second light source opposite the reflector.

37. The illumination unit according to any one of the illustrative embodiments 26 to 36, further comprises a light sensor positioned proximate the first light source and configured to monitor the intensity of the first light signal emitted from the first light source.

37. The illumination unit according to any one of the illustrative embodiments 26 to 37, further comprises a housing assembly that defines an internal space, wherein the first light source, the second light source, and the reflector are contained in the internal space of the housing assembly.

The invention claimed is:

1. An illumination unit, comprising:
a first light source positioned on a first axis, the first light source operable to generate a first light signal travelling on the first axis;
a second light source operable to generate a second light signal travelling on a second axis that intersects and is angularly offset with respect to the first axis; and
a reflector positioned at the intersection of the first axis and the second axis, the reflector including an aperture through which the first axis extends and a reflective surface angled with respect to the first axis and second axis, and
wherein the aperture is positioned to center the first light signal travelling therethrough on a target region located on the first axis opposite the first light source relative to the reflector, and wherein the reflective surface is configured to reflect the second light signal toward the target region.

2. The illumination unit according to claim 1, wherein the first light source is configured to generate a continuous spectrum of broadband white light.

3. The illumination unit according to claim 1, wherein the first light source is a light emitting diode.

4. The illumination unit according to claim 1, wherein the second light source is configured to generate a line spectrum.

5. The illumination unit according to claim 4, wherein the first angle is between 15 degrees and 75 degrees.

6. The illumination unit according to claim 1, wherein the second light source is a neon lamp.

7. The illumination unit according to claim 1, wherein the reflective surface is disposed along a reflector plane, the reflector plane and the first axis defining a first angle that is less than about 90 degrees.

8. The illumination unit according to claim 1, wherein the reflective surface is disposed along a reflector plane, the reflector plane and the second axis defining a second angle that is less than about 90 degrees.

9. The illumination unit according to claim 1, wherein the second angle is between 15 degrees and 75 degrees.

10. The illumination unit according to claim 1, wherein the first axis and the second axis intersect to define an angle that is between 45 degree and 135 degrees.

11. The illumination unit according to claim 1, wherein first light source and the second light source lie in a common plane that includes the first axis.

12. The illumination unit according to claim 1, further comprising:
a further reflector positioned adjacent to the second light source opposite the reflector.

13. The illumination unit according to claim 1, further comprising:
a light sensor positioned proximate the first light source and configured to monitor intensity of the first light signal emitted from the first light source.

14. The illumination unit according to claim 1, wherein the aperture is an elliptical aperture and the reflective surface is angled such that light traveling from the first light source though the aperture creates a circular beam of light.

15. The illumination unit according to claim 14, wherein the housing assembly includes a printed circuit board (PCB), the first light source and the second light source being mounted to the same PCB.

16. The illumination unit according to claim 14, further comprising positioning the first light source, the second light source, and the reflector in an internal space of a housing assembly.

17. The illumination unit according to claim 1, further comprising a lens positioned on the first axis opposite the reflector.

18. The illumination unit according to claim 1, further comprising a housing assembly that defines an internal space, wherein the first light source, the second light source, and the reflector are contained in the internal space of the housing assembly.

19. A method of forming an illumination unit, comprising:
positioning a first light source on a first axis, the first light source operable to generate a first light signal travelling on the first axis;
positioning a second light source on a second axis that intersects and is angularly offset with respect to the first axis, the second light source operable to generate a second light signal travelling on the second axis; and
positioning a reflector at the intersection of the first and second axes, the reflector including an aperture and a reflective surface, wherein the aperture is positioned such that the first axis extends through the aperture, and wherein the reflective surface is positioned to be angled with respect to the first axis and second axis, and
wherein the aperture is positioned to center the first light signal travelling therethrough on a target region located on the first axis opposite the first light source relative to the reflector, and wherein the reflective surface is configured to reflect the second light signal toward the target region.

20. The illumination unit according to claim 19, further comprising positioning a lens on the first axis opposite the reflector.

21. The illumination unit according to claim 19, wherein the first light source is configured to generate a continuous spectrum of broadband white light.

22. The illumination unit according to claim 19, wherein the second light source is a neon lamp.

23. The illumination unit according to claim 19, wherein the reflective surface is disposed along a reflector plane, the reflector plane and the first axis defining a first angle that is less than about 90 degrees.

24. The illumination unit according to claim 23, wherein the first angle is between 15 degrees and 75 degrees.

25. The illumination unit according to claim 19, wherein the reflective surface is disposed along a reflector plane, the reflector plane and the second axis defining a second angle that is less than about 90 degrees.

26. The illumination unit according to claim 19, wherein the second angle is between 15 degrees and 75 degrees.

27. The illumination unit according to claim 19, wherein the first axis and the second axis intersect to define an angle that is between 45 degree and 135 degrees.

28. The illumination unit according to claim 19, wherein first light source and the second light source lie in a common plane that includes the first axis.

29. The illumination unit according to claim 19, further comprising:
positioning another reflector adjacent to the second light source opposite the reflector.

30. The illumination unit according to claim 19, further comprising:
positioning a light sensor proximate the first light source, the light sensor being configured to monitor intensity of the first light signal emitted from the first light source.

* * * * *